US00PP35138P2

(12) United States Plant Patent
Robinson

(10) Patent No.: US PP35,138 P2
(45) Date of Patent: Apr. 25, 2023

(54) ***MISCANTHUS* PLANT NAMED 'RED ZENITH'**

(50) Latin Name: *Miscanthus sinensis*
Varietal Denomination: Red Zenith

(71) Applicant: Brian Robinson, Kinoulton (GB)

(72) Inventor: Brian Robinson, Kinoulton (GB)

( * ) Notice: Subject to any disclaimer, the term of this patent is extended or adjusted under 35 U.S.C. 154(b) by 0 days.

(21) Appl. No.: 17/747,192

(22) Filed: May 18, 2022

Related U.S. Application Data

(60) Provisional application No. 63/190,772, filed on May 19, 2021.

(51) Int. Cl.
*A01H 5/02* (2018.01)
*A01H 6/46* (2018.01)

(52) U.S. Cl.
USPC ..... Plt./384
CPC ..... *A01H 6/46* (2018.05)

(58) Field of Classification Search
USPC ..... Plt./384
CPC ..... A01H 6/46
See application file for complete search history.

(56) References Cited

U.S. PATENT DOCUMENTS

PP14,743 P2 * 5/2004 Speichert ..... A01H 6/46
Plt./384

OTHER PUBLICATIONS

UPOV and CPVO hit on a *Miscanthus* plant named, 'Red Zenith', QZ PBR 20210912, filed Mar. 30, 2021.*
Trademark to 'Red Zenith', U.S. Appl. No. 75/163,684, filed Sep. 10, 1996.*

* cited by examiner

*Primary Examiner* — Anne Marie Grunberg
(74) *Attorney, Agent, or Firm* — Penny J Aguirre

(57) ABSTRACT

A new cultivar of *Miscanthus sinensis* plant named 'Red Zenith' that is characterized by its exhibits a strong and vigorous plant habit, creating a v-shaped form tightly gathered at the base, its average plant height of 2 m, its foliage that is dark green in color with well-delineated white strips turning yellow striped in autumn, flowers that are vibrant red in sunlight with a pink sheen when young and fading to a paler red in late autumn, and its upright v-shaped flower tassels on thick peduncles.

2 Drawing Sheets

Botanical classification: *Miscanthus sinensis.*
Cultivar designation: 'Red Zenith'.

BACKGROUND OF THE INVENTION

The present invention relates to a new and distinct cultivar of *Miscanthus sinensis* and will be referred to hereafter by its cultivar name, 'Red Zenith'. 'Red Zenith' represents a new cultivar of Japanese silver grass, a cold hardy, perennial ornamental grass grown for landscape use.

'Red Zenith' was hand selected by the Inventor as a seedling from an open pollinated parent group of *Miscanthus* sinensis in Kinoulton, Northants, United Kingdom in May of 2015. The parentage is unknown.

Asexual propagation of the new cultivar was first accomplished by division by the Inventor in March of 2016 in Kinoulton, Northants, United Kingdom. Asexual propagation by division and tissue culture using meristematic tissue has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Red Zenith' as a unique cultivar of *Miscanthus.*

1. 'Red Zenith' exhibits a strong and vigorous plant habit, creating a v-shaped form tightly gathered at the base.
2. 'Red Zenith' exhibits an average plant height of 2 m.
3. 'Red Zenith' exhibits foliage that is dark green in color with well-delineated white strips turning yellow striped in autumn.
4. 'Red Zenith' exhibits flowers that are vibrant red in sunlight with a pink sheen when young and fading to a paler red in late autumn.
5. 'Red Zenith' exhibits upright v-shaped flower tassels on thick peduncles.

'Red Zenith' can be most closely compared to the sinensis cultivars 'China' (not patented) and 'EMPMIS01' (U.S. Plant Pat. No. 30,802). 'China' is similar to 'Red Zenith' in having red flowers and in being similar in height. 'China' differs from 'Red Zenith' in having thinner flower tassels on thinner peduncles that slightly droop and are lighter red in color. 'EMPMIS01' is similar to 'Red Zenith' in having flowers that are rich red in color. 'EMPMIS01' differs from 'Red Zenith' in having a spreading flower form and a shorter plant height.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Bally Robert Gardens, RHS Plants, Crocus, Vitro Westland, Provender Nurseries, Waitrose Garden, Genesis Plant Marketing Ltd, and Seiont Nurseries.

BRIEF DESCRIPTION OF THE DRAWINGS

The accompanying color photographs illustrate the overall appearance and distinct characteristics of the new *Miscanthus*. The photographs were taken in September of plants about 5 years in age as grown outdoors in a field in Kinoulton, Northants, United Kingdom.

The photograph in FIG. 1 provides a close-up view of the inflorescences of 'Red Zenith'.

Figure 1:
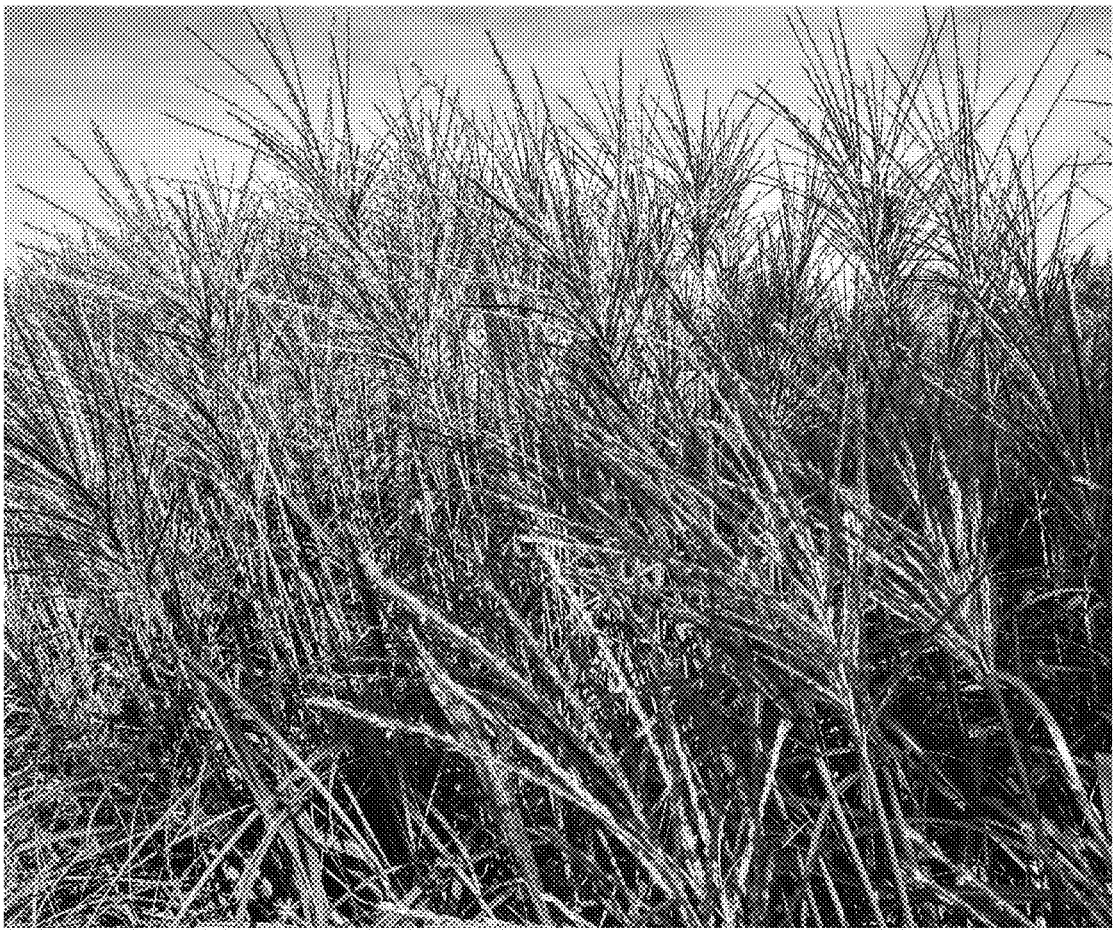
Figure 2:
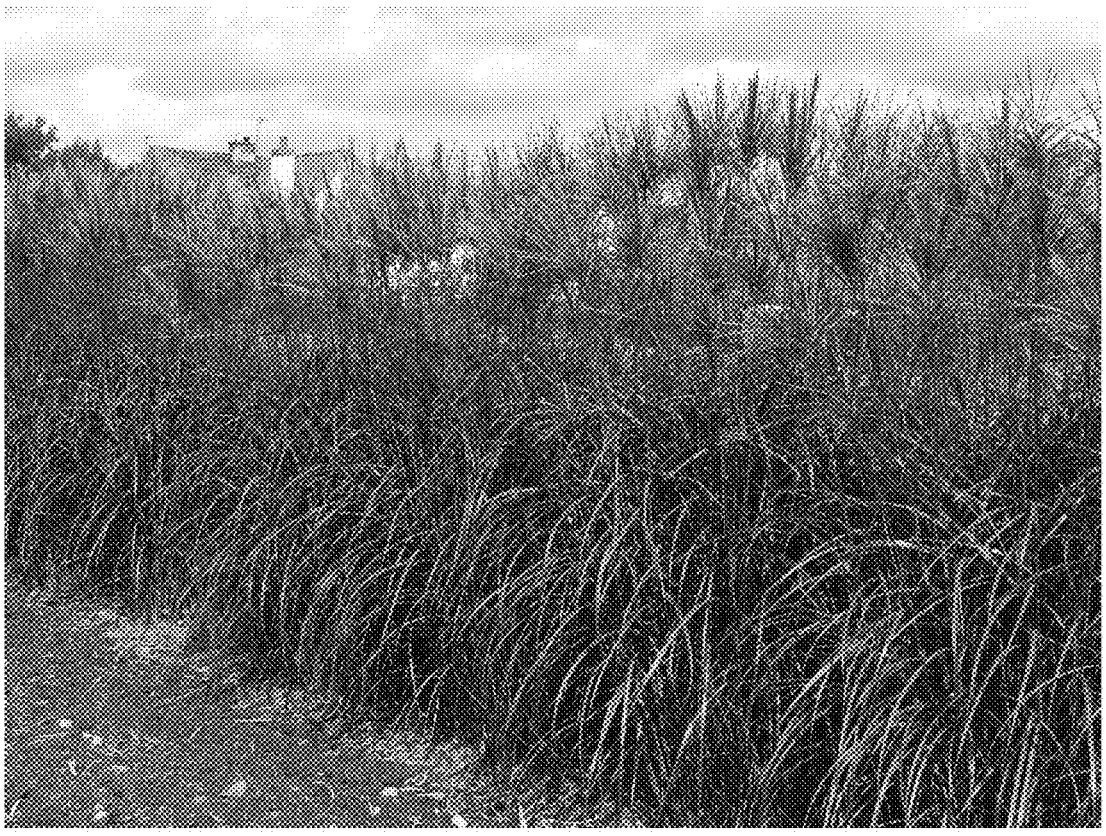

The photograph in FIG. 2 provides a view of a row of 'Red Zenith'.

The colors in the photograph are as close as possible with the photographic and printing technology utilized and the color values cited in the Detailed Botanical Description accurately describe the colors of the new *Miscanthus*.

DETAILED BOTANICAL DESCRIPTION

The following is a detailed description of 5-year-old plants of the new cultivar as grown outdoors in a field in Kinoulton, Northants, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms in early August through Autumn in the United Kingdom.

*Plant type*.—Herbaceous perennial grass.

*Plant habit*.—Clump-forming, upright and v-shaped (narrower at the base).

*Height and spread*.—Average of 2 m in height and 50 to 60 cm in diameter as a 5-year-old plant in the landscape.

*Hardiness*.—At least in U.S.D.A. Zones 5 to 9.

*Diseases and pests*.—No susceptibility or resistance to disease or pests has been observed.

*Root description*.—Thin fleshy, about N155A in color, no stolons or rhizomes present.

*Root development*.—An average of 2 weeks for root development in a liner from a division and an average of 4 weeks to produce a young rooted plant.

*Propagation*.—Division and tissue culture.

*Growth rate*.—Vigorous.

Culm (stem) description:

*General*.—Rounded, strong.

*Culm aspect*.—Growing from the base, held in an average angle of 5°.

*Culm quantity*.—Average of 30 basal shoots.

*Culm color*.—Young 145C, mature; N144C, mature internodes; N144C, finely mottled with N155A just below the internode, anthocyanin coloration absent at nodes.

*Culm size*.—Up to 73.6 cm in length, average of 5 mm in diameter.

*Culm internode length*.—7.3 cm.

*Culm surface*.—Moderately glossy, nodes are pubescent with a ring of adpressed short hairs; 1 mm in length, 155D in color.

*Culm pith*.—NN155C in color, 3 mm in thickness of straw cross section.

*Culm tillers*.—Not present.

Foliage description:

*Leaf shape*.—Linear.

*Leaf division*.—Simple.

*Leaf base*.—Sheathed, sheath 14.6 cm in length, 5 mm in width, 138B in color.

*Leaf apex*.—Narrow and long acuminate.

*Leaf aspect*.—Slightly carinate, tips twisted, leaves arching.

*Leaf venation*.—Parallel, only main vein is visible, upper side N155A, lower side 144A to 144B.

*Leaf margins*.—Smooth, very sharp when rubbed downwards due to very small sharp teeth.

*Leaf blade size*.—53.6 cm in length, 1.2 cm in width.

*Leaf (blade and sheath) surface*.—Both surfaces glabrous and smooth, upper surface moderately glossy, lower surface matte, no pubescence observed.

*Leaf ligules*.—Moderately pubescent with thin hairs, an average of 1.5 mm in length, 157A in color.

*Leaf number*.—An average of 11 per culm.

*Leaf arrangement*.—Alternate.

*Leaf blade color*.—Young upper surface; a blend of 143A and 146A, young lower surface; 138A, mature upper surface; a blend of 137B and 146A, mature lower surface; 137C, leaf flag; a blend of 143A and 146A, no anthocyanin present on basal leaf sheath.

*Auricles*.—Not observed.

*Flag leaves*.—Frequent.

*Collars*.—Not observed.

*Leaf buds*.—Not observed.

Flower description:

*General description*.—Compact, fan-shaped panicle (trullate) terminating from each stem, composed of numerous slender, silky aggregate cascading racemes of spikelets.

*Lastingness of inflorescence*.—Average of 1 month for spikelets to drop, rest of raceme persistent into winter.

*Fragrance*.—None.

*Panicle size*.—Up to 17.4 cm in length and 5.7 cm in width.

*Panicle color*.—A blend of 60C, 64C, and N155D.

*Flower number*.—An average of 240 flowers per inflorescence, 600 flowers per plant.

*Flower buds*.—An average of 5 mm in length, 2 mm in diameter, narrow ovate in shape, 145B in color, surface is moderately glossy and covered by fine extending hairs from the base of the floret 181A in color.

*Peduncle (rachis)*.—16.6 cm in length and 1.25 mm in width, moderately strong, held in a vertical angle, surface smooth and moderately glossy and 148A in color, no hairiness observed on convex surface of apical rachis.

*Pedicels.*—1 mm in length and 0.5 mm in width, moderately strong, held in an average angle of 5°, surface smooth and moderately glossy and 148B in color.

*Spikelet description* (*flowers*).—2 flowers per spikelet, an average of 5 mm in height and diameter, 8 mm in depth, consisting of 2 glumes, 1 palea, and 1 lemma, 2 glumes oppositely placed at the base of each individual flower, lemma and palea oppositely placed above the glumes, glumes; an average of 4 mm in length and 0.75 mm in width, lightly glossy and glabrous surface, ovate in shape, strongly concave, entire margins, cuneate base, narrowly acute apex, no venation visible, color; when opening and fully open glumes 163B to 163C, anthocyanin coloration absent, shoulder of lower glume slightly elevated, shape, length, beak, and hairiness of lower glume were not observed, glume bristles; 1 dense whorl of fine callus hairs extending from the base of the floret; 6 mm in length, 160D in color, no anthocyanin observed, lemma; an average of 8 mm in length and 0.5 mm in width, slightly glossy and glabrous surface, ovate in shape, strongly concave, entire margins, cuneate base, narrowly acute apex, no venation visible, not fading, color 162C, palea; an average of 4 mm in length and 0.75 mm in width, slightly glossy and glabrous surface, ovate in shape, strongly concave, entire margins, cuneate base, narrowly acute apex, no venation visible, not fading, color 162C, awn; linear in shape, 176B and 176C in color.

Reproductive organs:

*Androecium.*—Stamens; average of 2, anthers; narrow oblong in shape, 1.5 mm in length, 0.5 mm in width, 200B in color, filament; 4 mm in length, transparent and 160D in color, pollen; no pollen detected.

*Gynoecium.*—Pistil; 2, 2 mm in length, stigmas; plumose, 1 mm in length, 0.3 mm in diameter, 200A to 200B in color, style; 1 mm in length, 160D in color, ovary; 144A to 144B in color.

*Caryopsis.*—No caryopsis production was observed.

*Fertility.*—Self-incompatible (can only be outcrossed), no apomictis reproduction.

*Coleoptile anthocyanin.*—Not applicable (not seed grown).

*Vernalization.*—Not required.

It is claimed:

1. A new and distinct cultivar of *Miscanthus* plant named 'Red Zenith' as herein illustrated and described.

* * * * *